United States Patent [19]

Foncerrada et al.

[11] Patent Number: 5,277,905

[45] Date of Patent: Jan. 11, 1994

[54] **COLEOPTERAN-ACTIVE *BACILLUS THURINGIENSIS* ISOLATE**

[75] Inventors: Luis Foncerrada, San Diego; August J. Sick, Oceanside; Jewel M. Payne, San Diego, all of Calif.

[73] Assignee: Mycogen Corporation, San Diego, Calif.

[21] Appl. No.: 642,112

[22] Filed: Jan. 16, 1991

[51] Int. Cl.[5] .......................... A01N 63/00; C12N 1/20
[52] U.S. Cl. ................................. 424/93 L; 435/252.5
[58] Field of Search ...... 424/93 L; 195.1; 435/252.5, 832, 435/240.4; 800/205

[56] References Cited

U.S. PATENT DOCUMENTS 4,910,016 3/1990 Gaertner ........................... 424/93 L
4,966,765 10/1990 Payne et al. ....................... 424/93 L

FOREIGN PATENT DOCUMENTS 0202739 11/1986 European Pat. Off. .
0324254 7/1989 European Pat. Off. .
0337604 10/1989 European Pat. Off. .

OTHER PUBLICATIONS

Couch, T. L. (1980) "Mosquito Pathogenicity of *Bacillus thuringiensis var. israelensis,*" Developments in Industrial Microbiology 22:61–67.

Beegle, C. C. (1978) "Use of Entomogenous Bacteria in Agroecosystems," Developments in Industrial Microbiology 20:97–104.'

Krieg, A., A. M. Huger, G. A. Langenbruch, W. Schnetter (1983) "*Bacillus thuringiensis var. tenebrionis:* a new pathotype effective against Coleoptera larvae," Z. ang. Ent. 96:500–508.

*Primary Examiner*—Richard A. Schwartz
*Assistant Examiner*—Nancy T. Vogel
*Attorney, Agent, or Firm*—Saliwanchik & Saliwanchik

[57] ABSTRACT

The subject invention concerns a novel microbe and gene encoding a novel toxin protein with activity against insect pests of the order Coleoptera. Pests in the order Coleoptera do heavy damage to crops, e.g., corn. The novel *Bacillus thuringiensis* microbe of the invention is referred to as B.t. PS50C. The spores or crystals of this microbe, or mutants thereof, are useful to control coleopteran pests in various environments. The novel gene of the invention can be used to transform various hosts wherein the novel toxic protein can be expressed.

11 Claims, 2 Drawing Sheets

Figure 1 kDa

205

116
97

66

45

A B C

A. *Bacillus thuringiensis* PS86B1
B. *Bacillus thuringiensis* var. *san diego*
C. *Bacillus thuringiensis* PS50C

COLEOPTERAN-ACTIVE BACILLUS THURINGIENSIS ISOLATE

BACKGROUND OF THE INVENTION

*Bacillus thuringiensis* (B.t.) produces an insect toxin designated as δ-endotoxin. It is synthesized by the B.t. sporulating cell. The toxin, upon being ingested in its crystalline form by susceptible insect larvae, is transformed into biologically active moieties by the insect gut juice proteases. The primary target is insect cells of the gut epithelium, which are rapidly destroyed.

The reported activity spectrum of B.t. covers insect species within the order Lepidoptera, many of which are major pests in agriculture and forestry. The activity spectrum also includes the insect order Diptera, which includes mosquitos and black flies. See Couch, T.L. (1980) "Mosquito Pathogenicity of *Bacillus thuringiensis* var. *israelensis*," Developments in Industrial Microbiology 22:61–76; Beegle, C. C., (1978) "Use of Entomogenous Bacteria in Agroecosystems," Developments in Industrial Microbiology 20:97–104. Krieg, et al., Z. ang. Ent. (1983) 96:500–508, describe a B.t. isolate named *Bacillus thuringiensis* var. *tenebrionis*, which is reportedly active against two beetles in the order Coleoptera. These are the Colorado potato beetle, *Leptinotarsa decemlineata*, and *Agelastica alni*.

In European Patent Application 0 202 739 there is disclosed a novel B.t. isolate active against Coleoptera. It is known as *B. thuringiensis* var. *san diego* (B.t.sd.). U.S. Pat. No. 4,966,765 discloses the coleopteran-active *Bacillus thuringiensis* isolate B.t. PS86B1. European Patent Application 0 337 604 also discloses a novel B.t. isolate active against Coleoptera. This isolate is B.t. PS43F.

Coleopteran-active strains, such as B.t.sd., B.t. PS86B1, and B.t. PS43F, can be used to control foliar-feeding beetles. The Colorado potato beetle (*Leptinotarsa decemlineata*), for example, is susceptible to the delta-endotoxin of B.t.sd. and larvae are killed upon ingesting a sufficient dose of spore/crystal preparation on treated foliage.

A number of crops are attacked by flea beetles. These beetles belong to the family Chrysomelidae, the *decemlineata*. The adults can cause extensive damage by feeding on the foliage.

BRIEF SUMMARY OF THE INVENTION

The subject invention concerns a novel *Bacillus thuringiensis* (B.t.) isolate and a cloned gene therefrom which encodes a novel coleopteran-active protein. The novel B.t. isolate, known herein as *Bacillus thuringiensis* PS50C (B.t. PS50C), has thus far been shown to be active against the Colorado potato beetle (*Leptinotarsa decemlineata*). The novel δ-endotoxin gene of the invention encodes an ≈130 kDa protein.

The subject invention also includes mutants of B.t. PS50C which have substantially the same pesticidal properties as B.t. PS50C. Procedures for making mutants are well known in the microbiological art. Ultraviolet light and nitrosoguanidine are used extensively toward this end.

Further, the invention also includes the treatment of substantially intact B.t. PS50C cells, and recombinant cells containing the gene of the invention, to prolong the pesticidal activity when the substantially intact cells are applied to the environment of a target pest. Such treatment can be by chemical or physical means, or a combination of chemical or physical means, so long as the technique does not deleteriously affect the properties of the pesticide, nor diminish the cellular capability in protecting the pesticide. The treated cell acts as a protective coating for the pesticidal toxin. The toxin becomes available to act as such upon ingestion by a target insect.

BRIEF DESCRIPTION OF THE DRAWINGS

FIG. 1—Photograph of a Standard SDS Polyacrylamide Gel of B.t. PS50C, B.t.sd., and B.t. PS86B1.

DETAILED DISCLOSURE OF THE INVENTION

Figure 2:
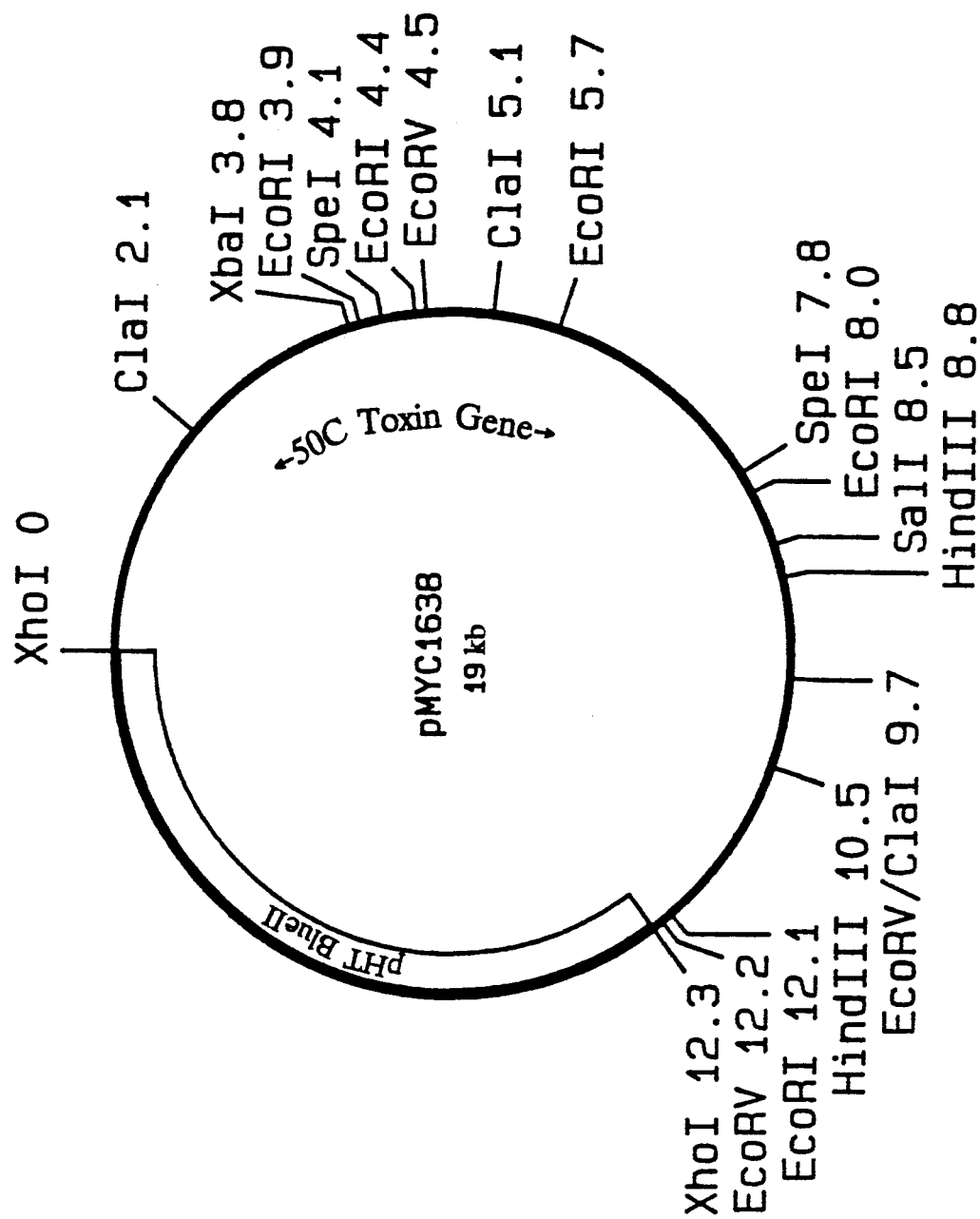
FIG. 2—Restriction map of pMYC1638.

The novel *Bacillus thuringiensis* isolate of the subject invention has the following characteristics in its biologically pure form:

Characteristics of B.t. PS50C

Colony morphology—Large colony, dull surface, typical B.t.

Vegetative cell morphology—typical B.t.

Culture methods—typical for B.t.

Flagellar serotyping—PS50C belongs to serotype 18, kumamotoensis.

Crystal morphology—a sphere.

RFLP analysis—Southern hybridization of total DNA distinguishes B.t. PS50C from B.t.sd. and other B.t. isolates.

Alkali-soluble proteins—SDS polyacrylamide gel electrophoresis (SDS-PAGE) shows a 130 kDa doublet protein.

A comparison of the characteristics of *B. thuringiensis* PS50C (B.t. PS50C) to the characteristics of the known B.t. strains *B. thuringiensis* var. *san diego* (B.t.sd.), *B. thuringiensis* PS86B1 (NRRL B-18299), and *B. thuringiensis* var. *kurstaki* (HD-1) is shown in Table 1.

TABLE 1

| | Comparison of B.t. PS50C, B.t. PS86B1, and B.t. HD-1 | | | |
|---|---|---|---|---|
| | B.t. PS50C | B.t.sd. | B.t. PS86B1 | B.t. HD-1 |
| Serovar | kumamotoensis | morrisoni | tolworthi | kurstaki |
| Type of inclusion | sphere | square wafer | flat, pointed ellipse, plus sm. inclusions | Bipyramid |
| Size of alkali-soluble proteins by SDS-PAGE | 130 kDa doublet | 72,000 64,000 | 75,000 68,000 61,000 | 130,000 68,000 |
| Host range | Coleoptera | Coleoptera | Coleoptera | Lepidoptera |

The cultures disclosed in this application have been deposited in the Agricultural Research Service Patent Culture Collection (NRRL), Northern Regional Research Center, 1815 North University Street, Peoria, Ill. 61604, USA.

| Culture | Repository No. | Deposit date |
|---|---|---|
| *Bacillus thuringiensis* PS50C | NRRL B-18746 | January 9, 1991 |
| *Escherichia coli* NM522 [pMYC1638] | NRRL B-18751 | January 11, 1991 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

B.t. PS50C, NRRL B-18746, can be cultured using standard art media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, liquid concentrate, granules, or other formulations by the addition of surfactants, dispersants, inert carriers and other components to facilitate handling and application for particular target pests. These formulation and application procedures are all well known in the art.

Plasmid DNA (pMYC1638) containing the toxin gene from B.t. PS50C can be purified from *E. coli* NM522[pMYC1638] by standard procedures well known in the art. The toxin gene can be excised from the plasmid DNA by restriction enzyme digestion, as indicated in FIG. 2.

Formulated products can be sprayed or applied onto foliage to control phytophagous beetles or caterpillars.

Another approach that can be taken is to incorporate the spores and crystals of B.t. PS50C into bait granules containing an attractant and applying these granules to the soil for control of soil-inhabiting Coleoptera. Formulated B.t. PS50C can also be applied as a seed-coating or root treatment or total plant treatment.

The B.t. PS50C cells can be treated prior to formulation to prolong the pesticidal activity when the cells are applied to the environment of a target pest. Such treatment can be by chemical or physical means, or by a combination of chemical and/or physical means, so long as the technique does not deleteriously affect the properties of the pesticide, nor diminish the cellular capability in protecting the pesticide. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride; alcohols, such as isopropyl and ethanol; various histologic fixatives, such as Bouin's fixative and Helly's fixative (See: Humason, Gretchen. L., Animal Tissue Techniques, W. H. Freeman and Company, 1967); or a combination of physical (heat) and chemical agents that prolong the activity of the toxin produced in the cell when the cell is applied to the environment of the target pest(s). Examples of physical means are short wavelength radiation such as gamma-radiation and X-radiation, freezing, UV irradiation, lyophilization, and the like.

The novel toxin gene of the subject invention was obtained from a novel coleopteran-active *B. thuringiensis* (B.t.) isolate designated B.t. PS50C. The gene was isolated as disclosed in the Examples.

The toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of coleopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganis are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti,*

*Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of ways are available for introducing the B.t. gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhances the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp., phylloplane organisms such as Pseudomonas sp., Erwinia sp. and Flavobacterium sp.; or such other organisms as Escherichia, Lactobacillus sp., Bacillus sp., Streptomyces sp., and the like. Specific organisms include *Pseudomonas aeruginosa, Pseudomonas fluorescens, Saccharomyces cerevisiae, Bacillus thuringiensis, Escherichia coli, Bacillus subtilis, Streptomyces lividans*, and the like.

The cell will usually be intact and be substantially in the proliferative form when treated, rather than in a spore form, although in some instances spores may be employed.

Treatment of the recombinant microbial cell can be done as disclosed infra. The treated cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bioavailability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the coleopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing B.t. PS50C, NRRL B-18746

A subculture of B.t. PS50C, NRRL B-18746 can be used to inoculate the following medium, a peptone, glucose, salts medium.

| | |
|---|---|
| Bacto Peptone | 7.5 g/l |
| Glucose | 1.0 g/l |
| KH$_2$PO$_4$ | 3.4 g/l |
| K$_2$HPO$_4$ | 4.35 g/l |
| Salt Solution | 5.0 ml/l |
| CaCl$_2$ Solution | 5.0 ml/l |
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |
| CaCl$_2$ Solution (100 ml) | |
| CaCl$_2$.2H$_2$O | 366 g |

| pH | 7.2 |
| --- | --- |

-continued

The salts solution and CaCl₂ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and crystals, obtained in the above fermentation, can be isolated by procedures well known in the art. A frequently-used procedure is to subject the harvested fermentation broth to separation techniques, e.g., centrifugation.

EXAMPLE 2

Testing of B.t. PS50C, NRRL B-18746 Spores and Crystals

B.t. PS50C, NRRL B-18746 spores and crystals are toxic to the Colorado potato beetle (CPB). The assay for the Colorado potato beetle was conducted as follows:

CPB Bioassay—Early second instar larvae of *Leptinotarsa decemlineata* are placed on potato leaves which have been dipped in suspensions containing *Bacillus thuringiensis* preparations. The larvae are incubated at 25° C. for 4 days, and larval mortality is recorded and analyzed using probit analysis.

EXAMPLE 3

Cloning of a Novel Toxin Gene from B.t. Isolate PS50C

Total cellular DNA was prepared from *Bacillus thuringiensis* (B.t.) cells grown to an optical density, at 600 nm, of 1.0. The cells were recovered by centrifugation and protoplasts were prepared in TES buffer (30 mM Tris-HCl, 10 mM EDTA. 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM (final concentration) neutral potassium chloride. The supernate was extracted twice with phenol/chloroform (1:1). Nucleic acids were precipitated with ethanol and DNA was purified by isopycnic banding on cesium chloride-ethidium bromide gradients.

Total cellular DNA from B.t. subsp. kumamotoensis (B.t.kum.), isolate PS50C, was digested with HindIII and fractionated by electrophoresis on a 0.8% (w/v) agarose-TAE (50 mM Tris-HCl, 20 mM NaOAc, 2.5 mM EDTA, pH=8.0) buffered gel. A Southern blot of the gel was hybridized with a [$^{32}$P]-radiolabeled oligonucleotide probe. Results showed that the hybridizing fragments of PS50C are approximately 12 Kb and 1.7 Kb in size.

A library was constructed from PS50C total cellular DNA partially digested with Sau3A and size fractionated by gel electrophoresis. The 9-23 Kb region of the gel was excised and the DNA was electroeluted and then concentrated using an Elutip-d ™ ion exchange column (Schleicher and Schuel, Keene, N.H.). The isolated Sau3A fragments were ligated into BamHI-digested LambdaGEM-11 ™ (PROMEGA). The packaged phage were plated on *E. coli* KW251 cells (PROMEGA) at a high titer and screened using the radiolabeled oligonucleotide probe. Hybridizing plaques were purified and rescreened at a lower plaque density. Single isolated, purified plaques that hybridized with the probe were used to infect *E. coli* KW251 cells in liquid culture for preparation of phage for DNA isolation. DNA was isolated by standard procedures. Preparative amounts of DNA were digested with XhoI (to release the inserted DNA from lambda sequences) and separated by electrophoresis on a 0.6% agarose-TAE gel. The large fragments were purified by ion exchange chromatography as above and ligated to XhoI-digested, dephosphorylated pHTBlueII (an *E. coli*/*B. thuringiensis* shuttle vector comprised of pBluescript s/k [Stratagene] and the replication origin from a resident B.t. plasmid [D. Lereclus et al. 1989. FEMS Microbiology Letters 60:211-218]). The ligation mix was introduced by transformation into competent *E. coli* NM522 cells (ATCC 47000) and plated on LB agar containing ampicillin, isopropyl-(β)-D-thiogalactoside (IPTG) and 5-bromo-4-chloro-4-indolyl-(β)-D-galactoside (XGAL). White colonies, with putative restriction fragment insertions in the (β)-galactosidase gene of pHTBlueII, were subjected to standard rapid plasmid purification procedures. Plasmids were analyzed by XhoI digestion and agarose gel electrophoresis. The desired plasmid construct, pMYC1638, contains an approximately 12 Kb XhoI insert. A partial restriction map (FIG. 2) of the cloned insert indicates that the toxin gene is novel compared to the maps of other toxin genes encoding insecticidal proteins.

Plasmid pMYC1638 was introduced into an acrystalliferous (Cry⁻) B.t. host (HD-1 cryB obtained from A. Aronson, Purdue University) by electroporation. Expression of an approximately 130 kDa protein was verified by SDS-PAGE. Broth containing spores and crystals was used for the determination of toxicity to *Leptinotarsa decemlineata*.

Plasmid pMYC1638 containing the B.t. toxin gene, can be removed from the transformed host microbe by use of standard well-known procedures. For example, *E. coli* NM522[pMYC1638] NRRL B-18751 can be subjected to cleared lysate isopycnic density gradient procedures, and the like, to recover pMYC1638.

EXAMPLE 4

Insertion of Toxin Gene Into Plants

The novel gene coding for the novel insecticidal toxin, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 5

Cloning of Novel *B. thuringiensis* Gene Into Baculoviruses

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399-406), and pAC380, described by Smith et al. (Smith, G. E., Summers, M. D. and Fraser, M. J. [1983] Mol Cell. Biol. 3:2156-2165). The gene coding for the novel protein toxin of the invention can be modified with BamHI linkers at appropriate regions both upstream and downstream from the coding region and inserted into the passenger site of one of the AcNPV vectors.

We claim:

1. A process for controlling coleopteran insect pests which comprises contacting said insect pests with an insect-controlling effective amount of *Bacillus thuringiensis* PS50C having the identifying characteristics of NRRL B-18746, or a mutant thereof.

2. A process, according to claim 1, wherein said insect pest is contacted with an insect-controlling sufficient amount of *Bacillus thuringiensis* PS50C, by incorporating said *Bacillus thuringiensis* PS50C into a bait granule and placing said granule on or in the soil when planting seed of a plant upon which plant insect pest is known to feed.

3. A process for controlling soil-inhabiting insect pests of the order Coleoptera which comprises (1) preparing a bait granule comprising *Bacillus thuringiensis* PS50C, or a mutant thereof, spores or crystals; and (2) placing said bait granule on or in the soil.

4. A process, according to claim 3, wherein said bait granule is applied at the same time corn seed is planted in the soil.

5. A process, according to claims 1 or 3, wherein substantially intact B.t. PS50C cells, or a mutant thereof, are treated to prolong the pesticidal activity when the substantially intact cells are applied to the environment of a target pest.

6. A composition of matter comprising *Bacillus thuringiensis* PS50C, or a mutant thereof, spores or crystals in association with an insecticide carrier.

7. A composition of matter, according to claim 6, wherein said carrier comprises beetle phagostimulants or attractants.

8. A composition of matter comprising *Bacillus thuringiensis* PS50C, or a mutant thereof, in association with formulation ingredients applied as a seed coating.

9. A biologically pure culture of *Bacillus thuringiensis* PS50C, having the identifying characteristics of NRRL B-18746, or a mutant thereof, having activity against insect pests of the order Coleoptera.

10. A process, according to claim 1, wherein the coleopteran pests are present on stored products.

11. A process, according to claim 1, wherein the coleopteran pest is the Colorado potato beetle.

* * * * *

UNITED STATES PATENT AND TRADEMARK OFFICE
CERTIFICATE OF CORRECTION

PATENT NO. : 5,277,905
DATED : January 11, 1994
INVENTOR(S) : Luis Foncerrada, et al It is certified that error appears in the above-indentified patent and that said Letters Patent is hereby corrected as shown below:

Column 2, line 53 (Table 1): After "PS86B1" insert --B.t.sd.--.

Column 4, lines 43-44: Delete "microorganis" and insert --microorganisms--.

Column 8, line 68: Delete "366 g" and insert --3.66 g--.

Column 9, line 37: After "EDTA" delete "." and insert --,--.

Signed and Sealed this

Eighth Day of November, 1994

Attest:

BRUCE LEHMAN

*Attesting Officer*  *Commissioner of Patents and Trademarks*